United States Patent

Aoshima et al.

[11] Patent Number: 5,827,807
[45] Date of Patent: Oct. 27, 1998

[54] ENAMEL REMOVER

[75] Inventors: Masayoshi Aoshima, Tokyo; Akira Shigeta, Ibaraki, both of Japan

[73] Assignee: Kao Corporation, Tokyo, Japan

[21] Appl. No.: 836,201

[22] PCT Filed: Nov. 9, 1995

[86] PCT No.: PCT/JP95/02286

§ 371 Date: May 15, 1997

§ 102(e) Date: May 15, 1997

[87] PCT Pub. No.: WO96/14823

PCT Pub. Date: May 23, 1996

[30] Foreign Application Priority Data

Nov. 16, 1994 [JP] Japan .................... 6-305759

[51] Int. Cl.⁶ .............. A61K 7/047; C11D 7/26
[52] U.S. Cl. ............ 510/118; 510/407; 510/437; 510/405; 134/38
[58] Field of Search .................. 510/118, 407, 510/437, 405; 134/38

[56] References Cited

U.S. PATENT DOCUMENTS

| | | | |
|---|---|---|---|
| 3,864,294 | 2/1975 | Busch | 260/28.5 |
| 4,594,111 | 6/1986 | Coonan | 134/3 |
| 4,735,798 | 4/1988 | Bernstein | 424/61 |
| 4,801,331 | 1/1989 | Murase . | |
| 4,992,262 | 2/1991 | Nakagaki et al. | 424/63 |
| 5,007,969 | 4/1991 | Doscher | 134/38 |
| 5,073,573 | 12/1991 | Schanz Martin et al. | 514/844 |
| 5,077,038 | 12/1991 | Hofmann . | |
| 5,098,594 | 3/1992 | Doscher | 252/162 |
| 5,427,710 | 6/1995 | Stevens | 252/166 |
| 5,486,305 | 1/1996 | Faryniarz et al. | 252/162 |
| 5,543,085 | 8/1996 | Miner | 510/118 |

FOREIGN PATENT DOCUMENTS 0 457 521  11/1991  European Pat. Off. .
7 17832  1/1995  Japan .

OTHER PUBLICATIONS

Patent Abstracts of Japan, vol. 013 No.579, Dec. 1989, JP A 01 242515.

Patent Abstracts of Japan, vol.013 No. 423 Sep. 1989, JP A 01 160908.

*Primary Examiner*—Douglas J. McGinty
*Attorney, Agent, or Firm*—Oblon, Spivak, McClelland, Maier & Neustadt, P.C.

[57] ABSTRACT

An enamel remover, which contains acetone, ethylene carbonate, and a monohydric lower alcohol at a specific ratio, has a notable effect for removing enamel painted on nails and has no stimulant odor in use. In addition, it does not damage nails or skin.

12 Claims, 1 Drawing Sheet

ENAMEL REMOVER

FIELD OF THE INVENTION

The present invention relates to an enamel remover, more specifically to an enamel remover which has a sufficient removing ability and which has no stimulant odor and gives no damages such as whitening to nails and skins.

DESCRIPTION OF THE RELATED ART

As for an enamel remover used for removing an enamel coated on nails, removers in which acetone, ethyl acetate, and butyl acetate are blended in large quantities have so far been widely used because of strong removing power thereof. However, because of a strong stimulant odor in the use thereof and a strong dehydrating power and degreasing power thereof, nails and skins are often damaged. Proposed in JP-A-7-17832 as a countermeasure therefore are an one containing propylene carbonate and aliphatic alcohol as main components and an enamel remover containing ethylene carbonate and monohydric lower alcohol as main components.

However, users usually paint enamel twice in order to prolong a life of the enamel on nails, and among them, some users paint the enamel three or more times one over another or use the enamel in combination with a base coat and a top coat. In such cases, it has been impossible to remove the enamel rapidly enough with conventional enamel removers.

JP-A-01 242 515 discloses a nail lacquer remover containing 40–60% propylene carbonate, 20–40 weight % ethanol, 0.1–5 weight % of hydroxypropyl cellulose and 0–40 weight % water as essential components. This composition is described as not damaging nails, not having a solvent smell and not raising the danger of ignition.

JP-A-01 160 908 reveals an enamel nail remover comprising 5.0–70.0 weight % acetone, 5.0–50.0 weight % water, 5.0–50.0 weight % propylene carbonate, 0.5–30.0 weight % liquid oil of hydrocarbon and 0.5–30.0 weight % hydrocarbon solvent.

In U.S. Pat. No. 4,801,331, a nail lacquer remover composition is disclosed which essentially consists of 30–65% by weight of a carbonate selected from ethylene carbonate, propylene carbonate, butylene carbonate and glycerine carbonate; 10–50% by weight of 1,3-dimethyl-2-imidizolidinone; 0.2–20% by weight of hydroxypropyl cellulose; and 13–40% by weight of water.

Accordingly, it has been desired to develop an enamel remover which satisfies sufficiently the above users and does not damage nails and skins and which has no stimulant odor in the use thereof.

SUMMARY OF THE INVENTION

Figure 1:
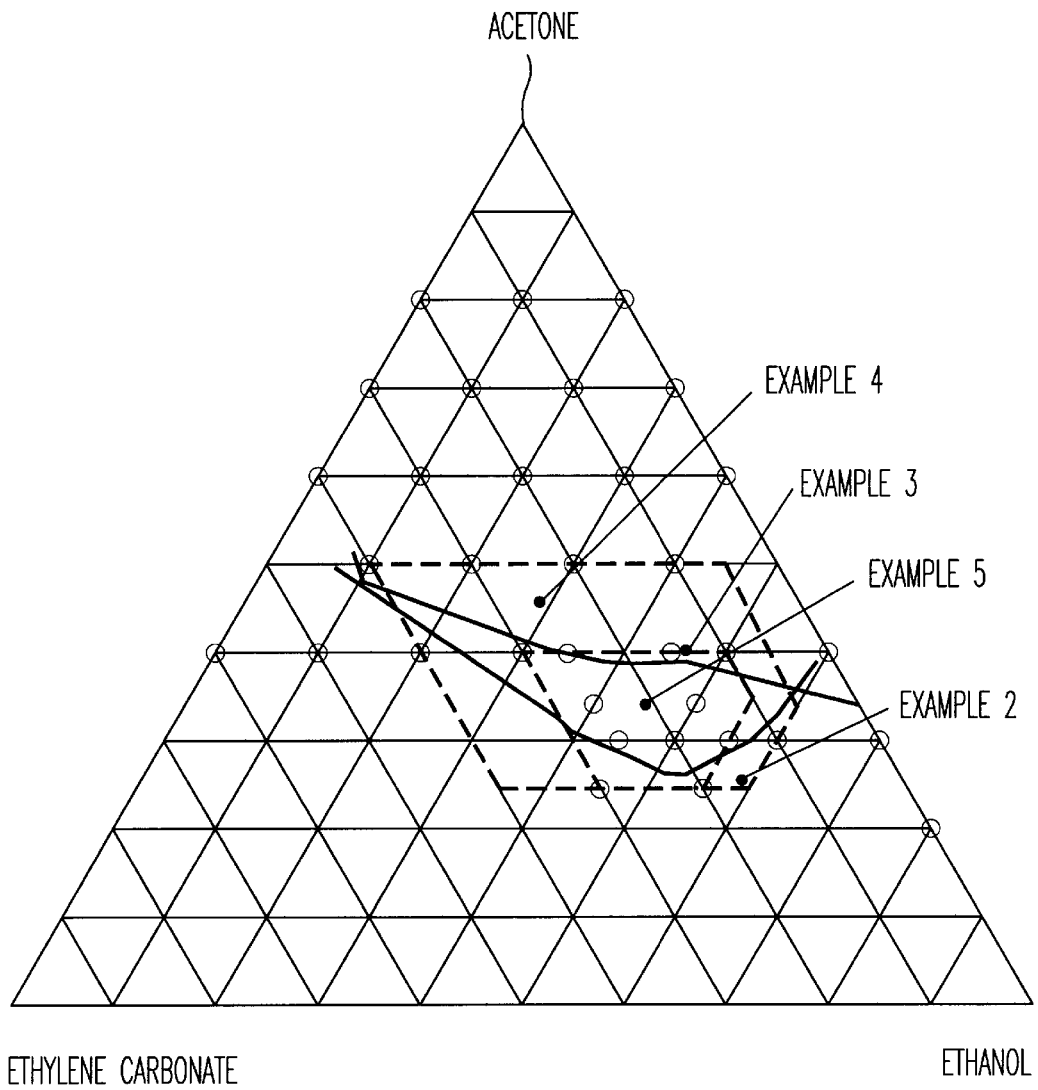
FIG. 1 is a drawing showing a preferred composition ratio of three structural elements of the composition of the present invention. The concentrations of the components shown in the drawing are the concentrations of the respective components, based on the whole amount of (A), (B) and (C).

Intensive investigations made by the present inventors in view of the above existing circumstances have resulted in finding that an enamel remover, which will be described below, provides remarkable advantages for removing enamel on nails and has no stimulant odor during the use thereof and that the nails and skins are not damaged thereby, and have come to complete the present invention.

The present invention provides an enamel remover characterized in that it contains acetone, ethylene carbonate, and monohydric $C_1$–$C_6$ alcohol and the combination thereof as essential components in a specific range makes it excellent in terms of a removing power, odor and prevention of damage of nails.

DETAILED DESCRIPTION OF THE INVENTION

The present invention provides an enamel remover composition comprising:

(A) ethylene carbonate or propylene carbonate,
(B) acetone, and
(C) monohydric $C_1$–$C_6$ alcohol, wherein contained are (A) in a proportion of 5 to 40 wt %, (B) acetone, and 25 to 50 wt % and (C) in a proportion of 10 to 60 wt %, based on the whole amount of (A)+(B)+(C).

Preferable contained are 10 to 30 wt % of (A) ethylene carbonate or propylene carbonate, 25 to 40 wt % of (B) acetone, and 30 to 55 wt % of (C) monohydric $C_1$–$C_6$ alcohol. This range of (A) is preferred from the viewpoint of the removing power. This range of (B) is preferred from the viewpoint of a good odor and a good feeling in touch. This range of (C) is preferred from the viewpoint of aftersensation after use.

these two composition ratios are shown by pentagons of chain lines, respectively, in the attached drawing. Particularly preferred is a composition ratio falling in a range surrounded by two curved solid lines in the attached drawing.

It is preferable that the component (A) is ethylene carbonate.

The monohydric $C_1$–$C_6$ alcohol component (C) includes ethanol, n-propanol, i-propanol, n-butanol, n-pentanol, and n-hexanol. Of them, ethanol, n-propanol and i-propanol are preferred, and ethanol is particularly preferred.

The present invention further provides a method for removing nail enamel from nails with the composition described above.

Further, the composition of the present invention contains water. The composition further contains at least one of an ester series oil component, polyols, and carbitols.

Water can be further blended into the enamel remover of the present invention in order to endow nails with a moisture retention property. Blending it in a proportion of 0.1 to 16%, preferably 0.5 to 5% can make nails moist.

An ester series oil component can be further blended into the enamel remover of the present invention in order to make up for an oil content of nails. To be concrete, there can be given glycerine esters such as triglyceride 2-ethylhexanoate, isostearylmyristoyl glyceride, and triacetin, diesters such as diisopropyl adipate, diisobutyl adipate, and dipropyl succinate, and aromatic esters such as diethyl phthalate and dibutyl phthalate.

Polyols and carbitols can be further blended into the enamel remover of the present invention in order to endow nails with a moisture retention property. To be concrete, there can be given glycerine, propylene glycol, 1,3-butylene glycol, and isoprene glycol as polyols, and ethyl carbitol and diethyl carbitol as carbitols.

The ester series oil component, polyols and carbitols each described above are blended into the enamel remover of the present invention so that the blending amount of one or two more of them is preferably 0.1 to 10%, particularly preferably 2 to 8%.

Components usually used for an enamel remover, for example, hydrocarbon series oil components such as liquid paraffin, silicon series oil components such as methyl polysiloxane, surfactants, various chemicals, perfumes, and dyes can be blended into the enamel remover of the present invention according to necessity as long as the effects of the present invention are not damaged.

The surfactants can be blended in order to improve a stability of the enamel remover of the present invention. Nonionic surfactants are preferred since they do not stimulate nails and skins, and the concrete examples thereof include linear secondary higher alcohols such as polyoxyethylene (hereinafter shown by "POE")-sec-tetradecyl ether, POE-glycerine fatty acid esters such as POE-glycerine monostearate and POE-glycerine tristearate, and POE-alkylphenyl ethers such as POE-octylphenyl ether and POE-nonylphenyl ether.

The enamel remover of the present invention is prepared by mixing the essential components described above by conventional method s and stirring evenly them.

The enamel remover of the present invention has a notable effect for removing enamel painted on nails and has no stimulant odor in the use thereof while containing acetone. It can display the performances described above without damaging nails and skins. The enamel remover of the present invention can favorably be used for removing every enamel such as nitrocellulose series enamel and aqueous enamel using an acrylic resin.

removed with the enamel removers obtained above to evaluate the odor and the removing power thereof according to the following criteria:

Evaluation Methods (1) Odor in the use

AA: Almost no odor

BB: Slight odor

CC: Stimulant odor

DD: Strong stimulant odor (2) Removing power (when nails are wiped off twice)

AA: Almost all enamel can be removed

BB: Slightly remains

CC: Fairly remains

DD: Scarcely removed

TABLE 2

|  | Example | | | | Comparative Example | | | | | | |
| --- | --- | --- | --- | --- | --- | --- | --- | --- | --- | --- | --- |
|  | 1 | 2 | 3 | 4 | 1 | 2 | 3 | 4 | 5 | 6 | 7 |
| Odor in use | AA | AA | BB | AA | AA | CC | DD | AA | AA | DD | DD |
| Removing power (painted once) | AA | AA | AA | AA | AA | AA | AA | AA | DD | AA | AA |
| Removing power (painted twice + top coat) | BB | AA | AA | AA | CC | AA | AA | CC | DD | AA | AA |

EXAMPLES

The present invention will concretely be explained below with reference to examples but the present invention will not be restricted thereto. Examples 1 to 4 and Comparative Examples 1 to 7

The enamel removers having the compositions shown in Table 1 were prepared by mixing evenly the respective components.

TABLE 1

| | Example | | | | Comparative Example | | | | | | | (%) |
| --- | --- | --- | --- | --- | --- | --- | --- | --- | --- | --- | --- | --- |
| Composition | 1 | 2 | 3 | 4 | 1 | 2 | 3 | 4 | 5 | 6 | 7 | |
| Acetone | 23 | 36 | 40 | 33 | — | 40 | 65 | — | 30 | 68 | 68 | |
| Ethylene carbonate | 14 | 13 | 23 | 20 | — | — | — | 30 | 65 | 25 | 17 | |
| Propylene carbonate | — | — | — | — | 75 | — | — | — | — | — | — | |
| Ethanol | 53 | 41 | 26 | 41 | 25 | 53 | 30 | 63 | — | — | 10 | |
| Glycerine | 3 | — | 3 | — | — | — | — | 3 | — | 2 | — | |
| 2-Ethylhexanoic acid triglyceride | — | 5 | — | 5 | — | 3 | 4 | 3 | — | — | — | |
| 1,3-Isostearyl-myristoyl diglyceride | 3 | — | 3 | — | — | 3 | — | — | 3 | 3 | 3 | |
| Water | 4 | 5 | 5 | 1 | — | 1 | 1 | 1 | 2 | 2 | 2 | |

An aqueous enamel (aqueous polymer emulsion: 90%) was painted once or twice on nails, and a top coat was further painted thereon. After 24 hours, the enamel was Example 5

An enamel remover having the composition shown below was prepared by mixing evenly the respective components.

TABLE 3

| Blend composition | (%) |
| --- | --- |
| Acetone | 36 |
| Ethylene carbonate | 10 |
| Propylene carbonate | 5 |
| Ethanol | 40 |
| Glycerine | 2 |
| Glyceryl tri-2-ethylhexanoate | 2 |
| Water | 5 |

Enamel was removed with the enamel remover obtained above to find that no stimulant odor was found in the use thereof and a good feeling was obtained. In addition, the above enamel remover did not cause whitening and damage on nails.

Example 6

An enamel remover having the composition shown below was prepared by mixing evenly the respective components.

TABLE 4

| Blend composition | (%) |
| --- | --- |
| Acetone | 31 |
| Ethylene carbonate | 15 |
| Propylene carbonate | 5 |
| Ethanol | 40 |
| Glycerine | 2 |
| Glyceryl tri-2-ethylhexanoate | 2 |
| Water | 5 |

Enamel was removed with the enamel remover obtained above to find that no stimulant odor was found in the use thereof and a good feeling was obtained. In addition, the above enamel remover did not cause whitening and damage on nails.

We claim:

1. An enamel remover composition, comprising:

(A) ethylene carbonate, (B) acetone, and (C) one or more monohydric $C_1$–$C_6$ alcohols, wherein contained are (A) in a proportion of from 5 to 40 wt %, (B) in a proportion of 25 to 50 wt %, and (C) in a proportion of 10 to 60 wt %, based on the total amount of (A)+(B)+(C).

2. The composition of claim 1, which comprises 10 to 30 wt % of (A), 25 to 40 wt % of (B) and 30 to 55 wt % of (C).

3. The composition of claim 2, wherein (C) is contained in an amount of 30 to 50 wt %.

4. The composition of claim 1, further comprising water.

5. The composition of claim 1, further comprising at least one of an ester oil component, polyol or carbitol.

6. The composition of claim 1, wherein said monohydric $C_1$–$C_6$ alcohol is selected from the group consisting of ethanol, n-propanol, i-propanol, n-butanol, n-pentanol and n-hexanol.

7. The composition of claim 6, wherein said monohydric $C_1$–$C_6$ alcohol is selected from the group consisting of ethanol, n-propanol and i-propanol.

8. The composition of claim 7, wherein said monohydric $C_1$–$C_6$ alcohol is ethanol.

9. The composition of claim 5, wherein said ester oil component is selected from the group consisting of triglyceride 2-ethylhexanoate, isostearylmyristoyl glyceride, triacetin, diisopropyl adipate, diisobutyl adipate and dipropyl succinate.

10. The composition of claim 5, wherein said polyol is selected from the group consisting of glycerine, propylene glycol 1,3-butylene glycol and isoprene glycol.

11. The composition of claim 7, wherein said carbitol is selected from the group consisting of ethyl carbitol and diethyl carbitol.

12. A method for removing enamel from nails, comprising applying the composition of claim 1, to nails.

* * * * *